(12) United States Patent
Olariu

(10) Patent No.: US 8,258,674 B2
(45) Date of Patent: Sep. 4, 2012

(54) SURFACE ACOUSTIC WAVE SENSOR AND SYSTEM

(76) Inventor: Viorel Olariu, Colorado Springs, CO (US)

(*) Notice: Subject to any disclaimer, the term of this patent is extended or adjusted under 35 U.S.C. 154(b) by 0 days.

(21) Appl. No.: 12/611,298

(22) Filed: Nov. 3, 2009

(65) Prior Publication Data
US 2011/0101822 A1     May 5, 2011

Related U.S. Application Data

(60) Provisional application No. 61/197,911, filed on Nov. 3, 2008.

(51) Int. Cl.
*H01L 41/08* (2006.01)

(52) U.S. Cl. ............ 310/313 R; 310/313 A; 310/313 B; 310/313 D

(58) Field of Classification Search .............. 310/313 R, 310/313 A, 313 B, 313 D, 367, 368, 36; 333/193–196
See application file for complete search history.

(56) References Cited

U.S. PATENT DOCUMENTS

| | | | | |
|---|---|---|---|---|
| 3,659,231 A | * | 4/1972 | De Vries | 333/194 |
| 5,565,725 A | * | 10/1996 | Nakahata et al. | 310/313 A |
| 6,339,365 B1 | * | 1/2002 | Kawase et al. | 333/193 |
| 6,650,205 B2 | * | 11/2003 | Goetz et al. | 333/193 |
| 6,710,514 B2 | * | 3/2004 | Ikada et al. | 310/313 C |
| 6,762,534 B2 | * | 7/2004 | Martin et al. | 310/313 B |

\* cited by examiner

*Primary Examiner* — Mark Budd

(74) *Attorney, Agent, or Firm* — Christensen O'Connor Johnson Kindness PLLC

(57) ABSTRACT

A surface acoustic wave sensor to measure physical, biological or chemical parameters is claimed. Using different piezoelectric substrate materials, piezoelectric substrates with different thicknesses or metallizations with different thicknesses or patterns are used to distinguish between the effects of different physical, biological or chemical parameters.

19 Claims, 4 Drawing Sheets

US 8,258,674 B2

SURFACE ACOUSTIC WAVE SENSOR AND SYSTEM

This application claims benefit of priority from U.S. Provisional Application No. 61/197,911, filed Nov. 3, 2008, which is incorporated herein by reference.

FIELD OF INVENTION

The present invention relates to a surface acoustic wave (SAW) device and more particularly to a surface acoustic wave (SAW) sensor to measure physical parameters such as temperature and strain.

BACKGROUND OF THE INVENTION

Surface acoustic wave (SAW) devices are widely used as band-pass filters or resonators. Surface acoustic wave (SAW) devices are electronic components that generate guided acoustic waves along the surface of the device. Any changes to the characteristics of the propagation path affect the velocity, phase or amplitude of the acoustic waves propagating along the surface of the device. These changes can easily be measured. The changes in frequency, phase or amplitude can be correlated to a physical quantity such as temperature, pressure or strain, or the detection of the presence of a specific gas. Thus, the device can be used as a sensor.

SAW sensors are very sensitive because the propagating acoustic wave has its energy concentrated close to the device surface. SAW devices are typically fabricated on single crystal anisotropic substrates that are also piezoelectric, such as quartz. A piezoelectric material produces electrical charges when it is subjected to mechanical stress. This phenomenon is reversible. A SAW sensor used to measure temperature, pressure, strain or the presence of a gas, typically includes a pair of spaced apart interdigital electrodes formed by a metal and disposed on the surface of the substrate. The interdigital electrode pair creates mechanical stress in the substrate when an electric field is applied. The (oscillatory) electric field creates a mechanical wave that propagates along the surface of the substrate. A second pair of interdigital electrodes converts the received mechanical wave back into an electric signal that is then compared to the original signal.

One of the difficulties of achieving acceptable performance parameters with SAW sensors is that quartz undergoes an $\alpha$ to $\beta$ transition at about 570° C. and loses its piezoelectric properties. Also, aluminum (Al), the most widely used metallization for SAW electrodes becomes soft when the temperature exceeds a few hundred degrees and actually melts at 660° C. For extended temperature ranges materials other than quartz have to be used. Materials such as LiNbO$_3$, materials from the LGX family of crystals or gallium phosphate can be used to extend the temperature range.

Another difficulty with SAW sensors is the fact that they cannot easily differentiate between different physical parameters. For example, a typical SAW sensor cannot easily distinguish between temperature and strain or temperature and pressure. Various physical parameters influence the propagation properties of a mechanical wave and the sensor cannot distinguish among them.

BRIEF SUMMARY OF THE INVENTION

The preferred embodiments of the present invention overcome the problems discussed, particularly the problem of distinguishing between the influences of various physical parameters on the properties of the SAW device. This is accomplished by using different substrates on parts of the device or by using different thicknesses of the substrate or the metalization layers. Also, different metallization ratios (i.e. different width to periodicity ratios) can be used to generate different SAW parameters that can be used to distinguish between different parameters. As will be shown in the detailed description of the different embodiments of the invention, this will affect the frequency behavior of the device differently and will allow the determination of temperature, strain, pressure or the presence of a specific gas separate from each other, thus distinguishing between these parameters.

Various objects and advantages of the present invention will become apparent to those skilled in the art from the following detailed description of the preferred embodiments, when read in light of the accompanying drawings.

BRIEF DESCRIPTIONS OF THE DRAWINGS

DETAILED DESCRIPTION OF THE PREFERRED EMBODIMENTS

Figure 1:
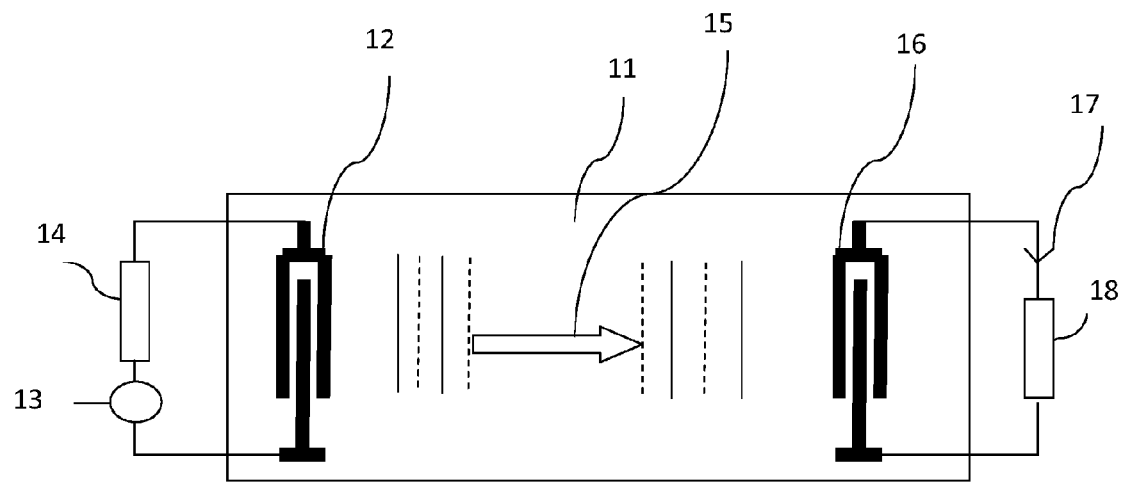
FIG. 1 is a schematic representation of a prior art surface acoustic wave (SAW) sensor with interdigital fingers.

Referring now to the drawings, FIG. 1 shows a prior art surface acoustic wave device that will be used to explain the functionality of such a device. On top of one of the surfaces of a piezoelectric substrate 11 an interdigital structure (IDT) 12 is formed that acts as a generator for a surface acoustic wave. Interdigital electrode structures in the form of interleaved fingers are typically used. The material of the piezoelectric substrate 11 is typically quartz, lithium niobate (LiNbO$_3$) or lithium tantalate (LiTaO$_3$). The piezoelectric substrate 11 can also be formed from a material of the LGX group (e.g. langasite, La$_3$Ga$_5$SiO$_{14}$), gallium phosphate (GaPO$_4$) or the like. These materials are particularly useful for high temperature operation since they do not exhibit a phase transition until very high temperatures (e.g. +1200° C. for langasite). The material of the interdigital structure 12 is typically aluminum (Al); however, other metals such as platinum (Pt), gold (Au), tungsten (W) or the like can also be used. The material for the interdigital structure is typically deposited by sputtering, vacuum evaporation, or chemical vapor deposition with a thickness of typically a fraction of a micron to several microns.

A (oscillatory) voltage 13 is applied to the interdigital structure 12. A series resistance 14 is usually present acting as a source resistance. The periodic voltage 13 applied to structure 12 generates periodic strain in the piezoelectric substrate that travels along the surface of the SAW device as a surface acoustic wave 15. The surface acoustic wave 15 interacts with a second interdigital structure 16 and is converted back into an electric signal that produces a current 17 that flows through a load impedance 18.

The distance between two fingers of the same polarity is termed the electrical period q of the IDT. The maximum electroacoustic interaction is obtained at the frequency $f_0$, the mid-frequency of the transducer. At this frequency the wavelength $\lambda_0$ of the surface acoustic wave precisely corresponds with the electrical period q of the IDT, so that all wave trains are superimposed in-phase and transmission is maximized $$q = \lambda_0 = v/f_0 \quad [1]$$

The relationship between the electrical and mechanical power density of a surface wave is described by the material-dependent piezoelectric coupling coefficient $k^2$. Around $k^{-2}$ overlaps of the transducer are required to convert the entire electrical power applied to the IDT into the acoustic power of a surface wave.

The velocity v of a surface wave on the substrate, and thus the propagation time $\tau$ and the mid-frequency $f_0$ of a surface wave component, can be influenced by a range of physical variables. In addition to temperature mechanical forces such as static elongation, compression, shear, bending and acceleration have a particular influence upon the surface wave velocity. This facilitates the remote interrogation of mechanical forces by surface wave sensors.

In general, the sensitivity S of the quantity x to a variation of the influence quantity y can be defined as:

$$S_y^x = \frac{1}{x}\frac{\partial x}{\partial y} \quad [2]$$

To first order, the influence of the quantity y (which can be temperature, strain et al.) on the mid-frequency $f_0$ and propagation time $\tau$ can be calculated as follows:

$$v(y) = v(y_0) \cdot [1 - S_y^v \cdot (y - y_0)] \quad [3]$$

$$f_0(y) = f_0(y_0) \cdot [1 - S_y^f \cdot (y - y_0)] \quad [4]$$

$$\tau(y) = \tau(y_0) \cdot [1 + S_y^\tau \cdot (y - y_0)] \quad [5]$$

Figure 2:
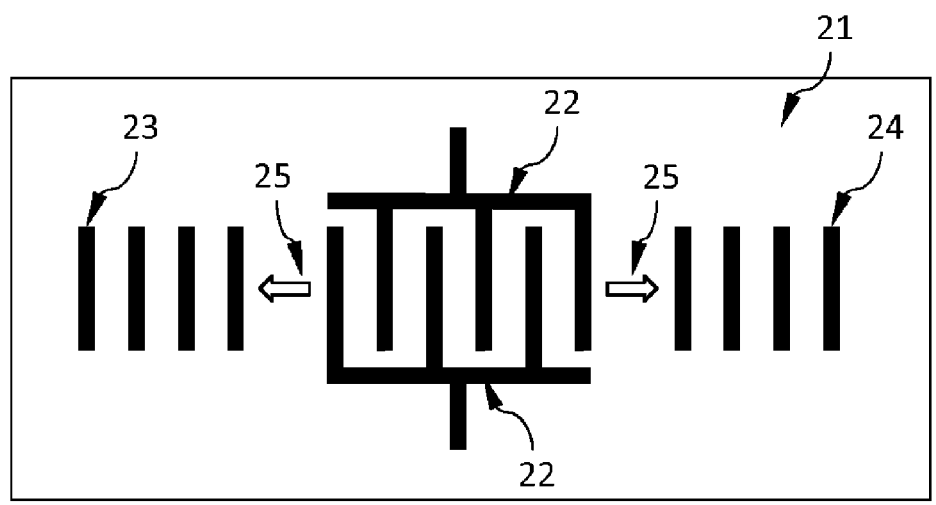
FIG. 2 is a schematic representation of a surface acoustic wave (SAW) sensor with reflectors.

FIG. 2 shows another type of surface acoustic wave (SAW) device. Here one set of an interdigital structure 22 is placed on one of the surfaces of a piezoelectric substrate 21. Reflectors 23 and 24 are placed a certain distance away from the interdigital structure 22 but on the same surface of the piezoelectric substrate 21. A (periodic) voltage applied to the interdigital structure 22 converts the electrical signal into a surface acoustic wave 25 that propagates along the substrate 21 and is reflected by the reflectors 23 and 24. Here the interdigital structure 22 converts the mechanical energy back into an electrical signal.

If only the differential propagation times or the differential phase between the individual reflected pulses are evaluated, the sensor signal is independent of the distance between the reader and the transponder. The differential propagation time $\tau_{2-1}$, and the differential phase $\phi_{2-1}$ between the two received pulses is obtained from the distance $L_{2-1}$ between the two reflectors, the velocity v of the surface wave, and the frequency f of the interrogation pulse.

$$\tau_{2-1} = \frac{2 \cdot L_{2-1}}{v}; \quad [6]$$

$$\varphi_{2-1} = 2\pi f \cdot \tau_{2-1} = \frac{4\pi f \cdot L_{2-1}}{v}$$

The measurable change $\Delta\tau_{2-1}$ or $\Delta\phi_{2-1}$ when a physical quantity y is changed by the amount $\Delta y$ is thus:

$$\Delta\tau_{2-1} = \tau_{2-1} \cdot S_y^\tau \cdot \Delta y; \quad \Delta\phi_{2-1} = 2\pi f \cdot \tau_{2-1} \cdot S_y^\tau \cdot \Delta y \quad [7]$$

The influence of the physical quantity y on the surface wave transponder can thus be determined only by the evaluation of the phase difference between the different pulses of the response signal.

In a reflective delay line the available path is used twice. However, if the IDT is positioned between two fully reflective structures, then the acoustic path can be used many more times due to multiple reflections. Such an arrangement is called a surface wave one-port resonator. The distance between the two resonators must be an integer multiple of the half wavelength $\lambda_0$ at the resonant frequency $f_1$. The displacement of the mid-frequency $\Delta f_1$ and the displacement of the associated phase $\Delta\phi_1$ of a resonator due to a change of the physical quantity y with loaded Q factor are:

$$\Delta f_1 = -f_1(y_0) \cdot S_y^f \cdot \Delta y; \quad [8]$$

$$\Delta\varphi = 2Q \cdot \frac{\Delta f_1}{f_1}$$

where $f_1$ is the unaffected resonant frequency of the resonator.

From the equations above it is obvious that the influence quantity y can be estimated by measuring time delay ($\tau$), phase ($\phi$), or frequency (f) variation. Temperature, strain, and other parameters can be measured with very good accuracy (0.1° C., 0.1 µstrain, etc.) at very high rate ($10^5$ measurements per second).

Figure 3:
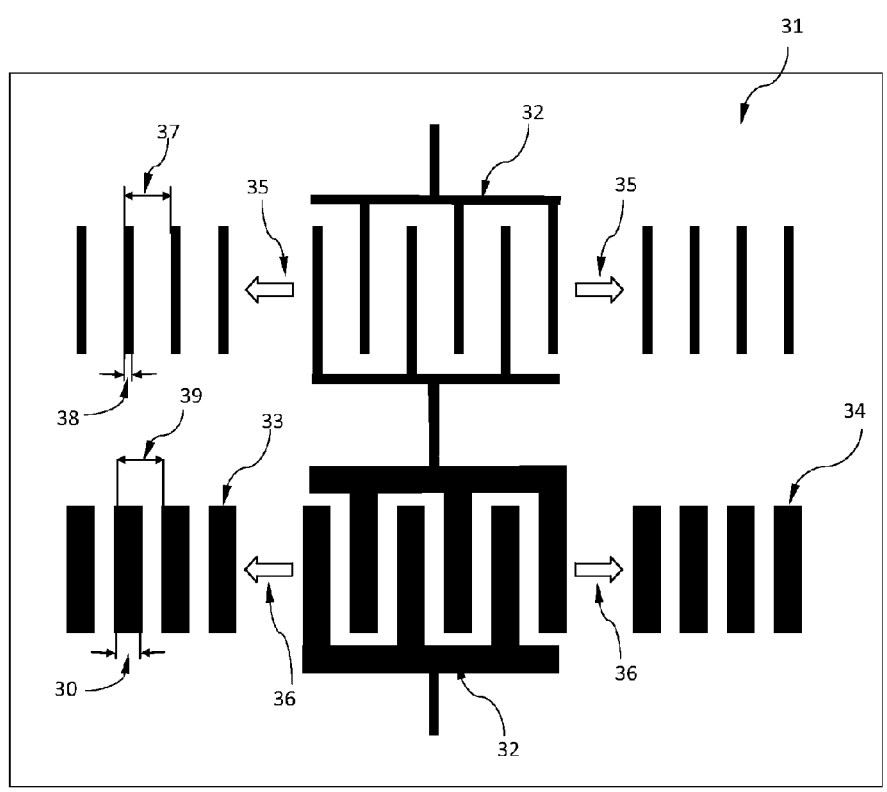
FIG. 3 is a schematic representation of a surface acoustic wave (SAW) sensor with different metallization ratios to separate the effect of temperature and strain.

FIG. 3 shows a specific embodiment of the current invention with two SAW sensors arranged in parallel with different metalization ratios. Similar to the structure shown in FIG. 1 each SAW sensor in FIG. 3 is formed with an interdigital structure (IDT) 32 on top of one of the surfaces of a piezoelectric substrate 31 which serves as a generator for a surface acoustic wave. The interdigital structures of the two different SAW sensors have the same periodicity 37/39 that determines the frequency of the device. However, the width 30 and 38 of the fingers of the IDTs 32 are quite different. The propagation properties of a SAW sensor depend on the ratio of the width 30 and 38 to the periodicity 37 and 39 and are used to distinguish between the different physical, biological or chemical effects.

Figure 4:
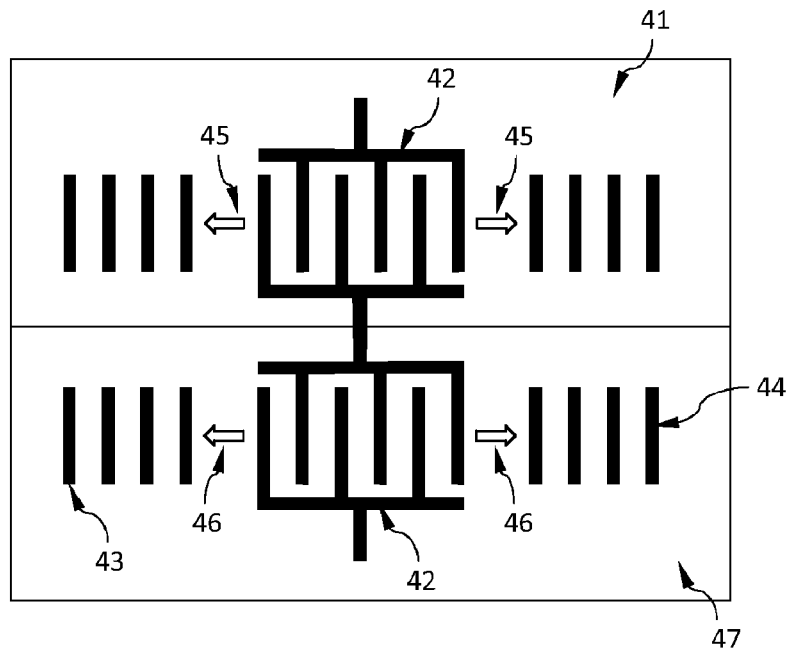
FIG. 4 is a schematic representation of one embodiment of a surface acoustic wave (SAW) sensor to separate the effect of temperature and strain based on sensor devices with different substrates.

FIG. 4 shows another embodiment of the current invention. Two sensors are built on different substrate materials 41 and 47. Material 41, for example, is quartz, whereas substrate 47, for example, is lithium niobate. According to equations [1]-[8] the effects of strain and temperature can be separated since the basic properties of SAW propagation depend on the substrate parameters. Since the substrates are different, the basic properties of SAW propagation are different and enough variables exist to separate strain and temperature effects in equations [1]-[8].

Figure 5:
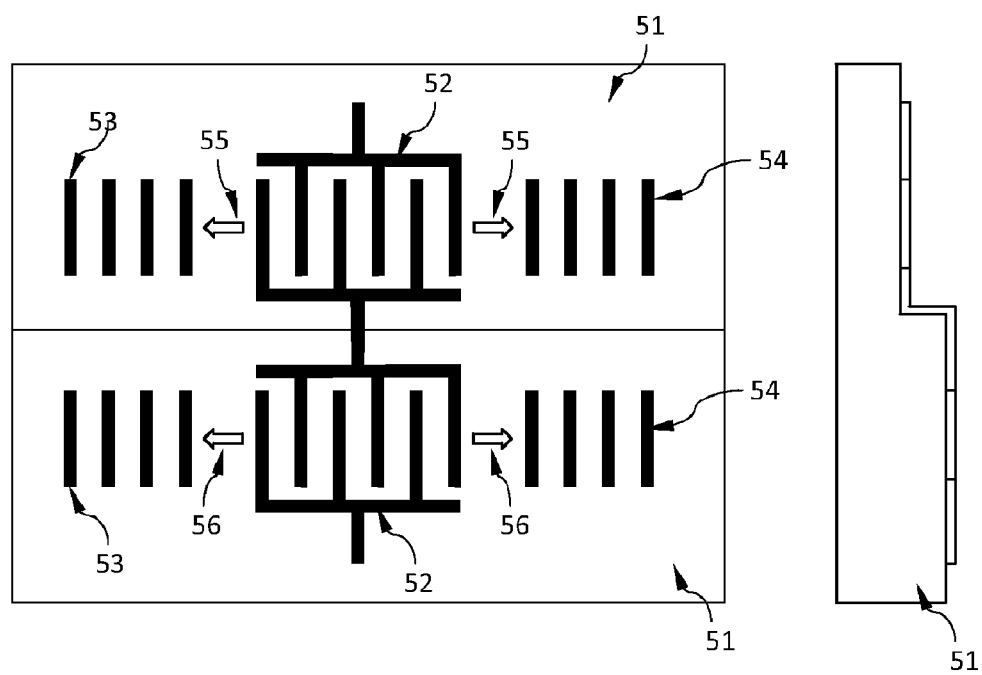
FIG. 5 is a schematic representation of an embodiment of a surface acoustic wave (SAW) sensor to separate the effect of temperature and strain based on different thicknesses of the piezoelectric substrate.

It is known that the SAW propagation parameters depend on the thickness of the piezoelectric substrate. FIG. 5 shows an embodiment of the current invention where a portion of the piezoelectric substrate 51 is thinner than the other portion.

Interdigital structures 52 are placed on the thinner and thicker portion of the device. Reflectors 53 and 54 are placed a certain distance away from the interdigital structures 52. Surface acoustic waves 55 and 56 are generated by the interdigital structures 52 that travel along the surface of substrate 51 and are reflected by the reflectors 53 and 54. Since the basic SAW propagation parameters depend on the thickness of substrate 51 enough variables are available to solve equations [1]-[8] for strain and temperature independently.

Figure 6:
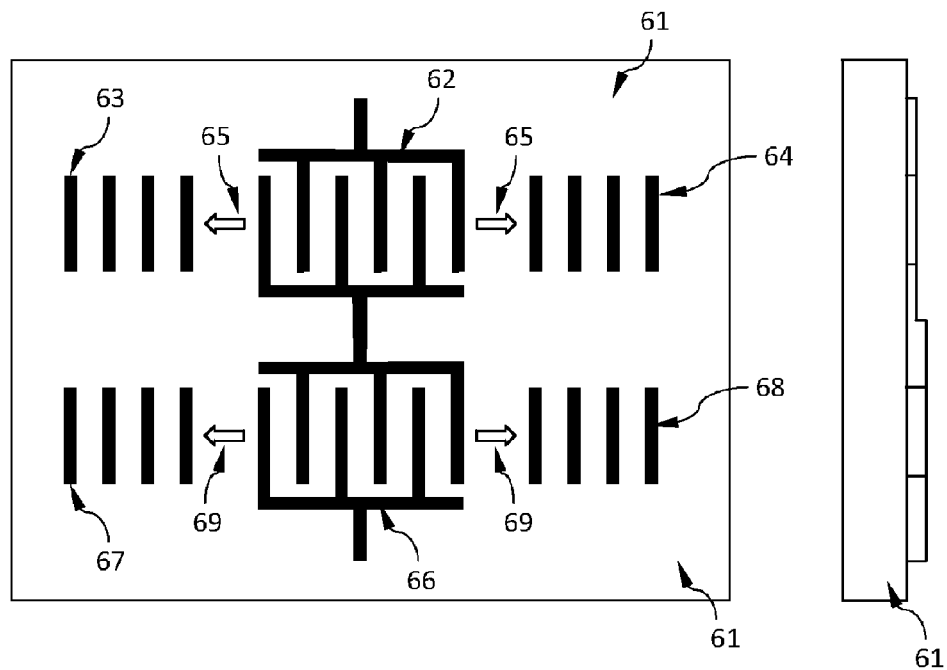
FIG. 6 is a schematic representation of an embodiment of a surface acoustic wave (SAW) sensor to separate the effect of temperature and strain based on different thicknesses of the metallization.

It is also known that the basic SAW propagation parameters depend on the thickness of the metallization, i.e. the thickness of the interdigital structures and the reflectors. FIG. 6 shows an embodiment of the current invention where two sets of interdigital structures 61 and 66 with different thickness are placed on one of the surfaces of a piezoelectric substrate 61 with constant thickness. Two sets of reflectors 63,64 and 67,68 are placed a certain distance away from the interdigital structures 62 and 66. The thickness of reflectors 63 and 64 is equal to or close to the thickness of interdigital structure 62 whereas the thickness of reflectors 67 and 68 is equal to or close to the thickness of interdigital structure 66. Since the basic SAW propagation parameters depend on the thickness of the interdigital structures 62 and 66 and the reflectors 63 and 64, or 67 and 68, enough variables are available to solve equations [1]-[8] for strain and temperature independently.

Figure 7:
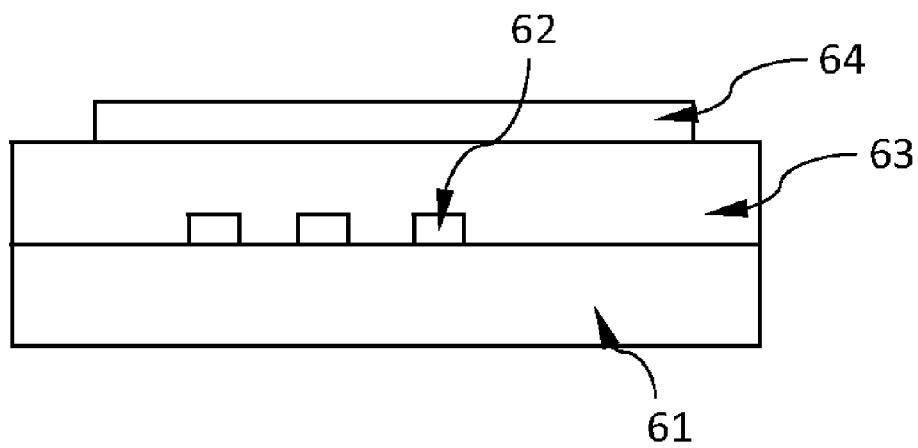
FIG. 7 is a schematic representation of an embodiment of a surface acoustic wave (SAW) sensor with a layered structure.

FIG. 7 shows an embodiment of the current invention where the interdigital structure 72 is placed on the surface of a backing plate 73. The material of the backing plate is non-piezoelectric. A piezoelectric layer 71 serving as the substrate is placed on top of the interdigital structure 72. This piezoelectric layer 71 is preferably a polycrystalline layer of a material such as zinc oxide (ZnO). An additional conductive layer 72 is placed on top of the structure.

The above detailed descriptions of embodiments of the invention are not intended to be exhaustive or to limit the invention to the precise form disclosed above. While specific embodiments of, and examples for, the invention are described above for illustrative purposes, various equivalent modifications are possible within the scope of the invention, as those skilled in the relevant art will recognize. The teachings of the invention provided herein can be applied to other systems, not necessarily to the SAW sensor systems described above. These and other changes can be made to the invention in light of the detailed description. Furthermore, the elements and acts of the various embodiments above can be combined to provide further embodiments beyond those described.

The invention claimed is:

1. A surface acoustic wave sensor system, comprising:
   (a) a first piezoelectric device, comprising:
      (i) a first piezoelectric substrate; and
      (ii) a first electrode pattern disposed on the first piezoelectric substrate;
      wherein the first electrode pattern is spaced apart and defines a first detection region on a surface of the first piezoelectric substrate intermediate the first electrode pattern;
      wherein the first electrode pattern is configured to generate and detect a first surface acoustic wave signal that travels through the first detection region; and
   (b) a second piezoelectric device, comprising:
      (i) a second piezoelectric substrate, formed from a different piezoelectric material than the first piezoelectric substrate; and
      (ii) a second electrode pattern disposed on the second piezoelectric substrate;
      wherein the second electrode pattern is spaced apart and defines a second detection region on a surface of the second piezoelectric substrate intermediate the second electrode pattern;
      wherein the second electrode pattern is configured to generate and detect a second surface acoustic wave signal that travels through the second detection region; and
   wherein the sensor system is configured to detect a change in a physical condition between the first detection region and the second detection region by comparing the first surface acoustic wave signal to the second acoustic wave signal.

2. The surface acoustic wave sensor of claim 1, further comprising a non-piezoelectric support layer with the first electrode pattern disposed on said non-piezoelectric support layer, said first piezoelectric substrate placed on top of said conductive layer and a second conductive layer placed on top of said first piezoelectric substrate.

3. The surface acoustic wave sensor of claim 1, wherein the material of the first piezoelectric substrate is selected from the group consisting of quartz, lithium niobate ($LiNbO_3$), lithium tantalate ($LiTaO_3$), gallium phosphate ($GaPO_4$), zinc oxide (ZnO), and materials from the LGX group of materials.

4. The surface acoustic wave sensor of claim 3, wherein one of said piezoelectric substrates is selected from the group consisting of langasite ($La_3Ga_5SiO_{14}$) and langatate ($La_3Ga_{5.5}Ta_{0.5}O_{14}$).

5. The surface acoustic wave sensor of claim 1, wherein the material of the first piezoelectric substrate is a piezoelectric polymer.

6. The surface acoustic wave sensor of claim 1, wherein the material of the first piezoelectric substrate is a piezoelectric ceramic.

7. The surface acoustic wave sensor of claim 6, wherein the material of the first piezoelectric substrate is selected from the group consisting of lead zirconate titanate (PZT), strontium bismuth titanate (SBT) and barium strontium titanate (BST).

8. The sensor system of claim 1, wherein the change in the physical condition is selected from the group consisting of temperature change, strain change, and exposure to a chemical or biological analyte.

9. The sensor system of claim 1, wherein the first detection region and the second detection region are exposed to an environment surrounding the sensor system so as to allow a chemical or biological analyte to be detected.

10. A surface acoustic wave sensor system, comprising:
   (a) a first piezoelectric device, comprising:
      (i) a piezoelectric substrate; and
      (ii) a first electrode pattern disposed on the piezoelectric substrate;
      wherein the first electrode pattern is spaced apart and defines a first detection region on a surface of the piezoelectric substrate intermediate the first electrode pattern;
      wherein the first electrode pattern has a first width;
      wherein the first electrode pattern is configured to generate and detect a first surface acoustic wave signal that travels through the first detection region; and
   (b) a second piezoelectric device, comprising a second electrode pattern disposed on the piezoelectric substrate;
      wherein the second electrode pattern is spaced apart and defines a second detection region on a surface of the piezoelectric substrate intermediate the second electrode pattern;
      wherein the second electrode pattern has a second width that is different than the first width;

wherein the second electrode pattern is configured to generate and detect a second surface acoustic wave signal that travels through the second detection region; and wherein the sensor system is configured to detect a change in a physical condition between the first detection region and the second detection region by comparing the first surface acoustic wave signal to the second acoustic wave signal.

11. The sensor system of claim 10, wherein the change in the physical condition is selected from the group consisting of temperature change, strain change, and exposure to a chemical or biological analyte.

12. The sensor system of claim 10, wherein the first detection region and the second detection region are exposed to an environment surrounding the sensor system so as to allow a chemical or biological analyte to be detected.

13. A surface acoustic wave sensor system, comprising:
(a) a first piezoelectric device, comprising:
  (i) a piezoelectric substrate; and
  (ii) a first electrode pattern disposed on the piezoelectric substrate;
  wherein the first electrode pattern is spaced apart and defines a first detection region on a surface of the piezoelectric substrate intermediate the first electrode pattern;
  wherein the first electrode pattern has a first thickness;
  wherein the first electrode pattern is configured to generate and detect a first surface acoustic wave signal that travels through the first detection region; and
(b) a second piezoelectric device, comprising a second electrode pattern disposed on the piezoelectric substrate;
  wherein the second electrode pattern is spaced apart and defines a second detection region on a surface of the piezoelectric substrate intermediate the second electrode pattern;
  wherein the second electrode pattern has a second thickness that is different than the first thickness;
  wherein the second electrode pattern is configured to generate and detect a second surface acoustic wave signal that travels through the second detection region; and
  wherein the sensor system is configured to detect a change in a physical condition between the first detection region and the second detection region by comparing the first surface acoustic wave signal to the second acoustic wave signal.

14. The sensor system of claim 13, wherein the change in the physical condition is selected from the group consisting of temperature change, strain change, and exposure to a chemical or biological analyte.

15. The sensor system of claim 13, wherein the first detection region and the second detection region are exposed to an environment surrounding the sensor system so as to allow a chemical or biological analyte to be detected.

16. The surface acoustic wave sensor of claim 13, wherein the material of said piezoelectric substrate is selected from the group consisting of quartz, lithium niobate ($LiNbO_3$), lithium tantalate ($LiTaO_3$), gallium phosphate ($GaPO_4$), zinc oxide (ZnO), and materials from the LGX group of materials.

17. The surface acoustic wave sensor of claim 16, wherein the material of said piezoelectric substrate is selected from the group consisting of langasite ($La_3Ga_5SiO_{14}$) and langatate ($La_3Ga_{5.5}Ta_{0.5}O_{14}$).

18. The surface acoustic wave sensor of claim 10, wherein the material of said piezoelectric substrate is selected from the group consisting of quartz, lithium niobate ($LiNbO_3$), lithium tantalate ($LiTaO_3$), gallium phosphate ($GaPO_4$), zinc oxide (ZnO), and materials from the LGX group of materials.

19. The surface acoustic wave sensor of claim 18, wherein the material of said piezoelectric substrate is selected from the group consisting of langasite ($La_3Ga_5SiO_{14}$) and langatate ($La_3Ga_{5.5}Ta_{0.5}O_{14}$).

* * * * *